United States Patent [19]

Hiltebrandt et al.

[11] 4,207,887
[45] Jun. 17, 1980

[54] GAS INSUFFLATION APPARATUS

[75] Inventors: Siegfried Hiltebrandt, Knittlingen; Helmut Wurster, Oberderdingen, both of Fed. Rep. of Germany

[73] Assignee: Richard Wolf GmbH, Knittlingen, Fed. Rep. of Germany

[21] Appl. No.: 919,375

[22] Filed: Jun. 26, 1978

Related U.S. Application Data

[63] Continuation of Ser. No. 729,167, Oct. 4, 1976, abandoned.

[30] Foreign Application Priority Data

Jun. 1, 1977 [FR] France .............................. 77 16683

[51] Int. Cl.² .......................................... A61M 13/00
[52] U.S. Cl. ........................... 128/207.28; 128/204.23
[58] Field of Search ............ 128/184, 172, 188, 145.5, 128/145.6, 145.8, DIG. 17, DIG. 12, 351, 213 R, 260

[56] References Cited

U.S. PATENT DOCUMENTS

| 2,830,580 | 4/1958 | Saklad et al. | 128/DIG. 17 |
| 3,251,361 | 5/1966 | Rusz | 128/188 |
| 3,794,026 | 2/1974 | Jacobs | 128/145.8 |
| 3,870,072 | 3/1975 | Lindemann | 128/184 |
| 3,885,590 | 5/1975 | Ford et al. | 128/184 |
| 3,982,533 | 9/1976 | Wiest | 128/184 |

Primary Examiner—Henry J. Recla
Attorney, Agent, or Firm—Kinzer, Plyer, Dorn & McEachran

[57] ABSTRACT

Insufflation gas from a compressed gas source is introduced into a body cavity through a tube connected to the source by an insufflation duct, the pressure in the body cavity being measured by a pressure gauge connected to the body cavity by a measuring duct, and any deviations from a preselected gas pressure for the body cavity being sensed in the measuring duct by control means operative to open or close a valve in the insufflation duct to control the pressure of the gas in the body cavity.

15 Claims, 3 Drawing Figures

GAS INSUFFLATION APPARATUS

This is a continuation, of application Ser. No. 729,167, filed Oct. 4, 1976 now abandoned.

BACKGROUND OF THE INVENTION

Field of the Invention

The invention relates to a gas insufflation apparatus for filling body cavities with gas, in which the gas, whose pressure can be set at a desired level, is fed from a source of compressed gas via an insufflation duct to a canula or the like which is to be inserted in the body cavity.

An object of the invention is to make it possible for a doctor to preset as desired the pressure of the volume of gas to be produced in the body cavity to suit the requirements of the patient to be examined, or in other words to preselect a pneumatic pressure which is specific to the patient and which is then automatically monitored and regulated.

Another object of the invention is to set off an alarm as soon as the pressure of gas in the body cavity reaches or exceeds a critical level.

SUMMARY OF THE INVENTION

The invention consists in the case of a gas insufflation apparatus of the kind initially described, in connecting the body cavity via a measuring duct to a pressure gauge and having the gas pressure in the body cavity actuate, either directly or via the pressure gauge, controller for opening and closing a valve in the insufflation duct, which controller responds to divergences in the body cavity from the pressure laid down. This makes it possible for the doctor to preselect the intracorporeal pressure in the body cavity to give the particular pneumatic pressure specific to the patient and for this pressure to be maintained under automatic control.

To control the valve in the insufflation duct, and thus to maintain a fixed gas pressure in the body cavity, it is possible to use an adjustable pneumatic pressure switch which responds to gas pressure in the body cavity. It is however also possible to make the valve in the insufflation duct a solenoid valve and to use as the pressure gauge a contact-equipped pressure gauge by which the solenoid valve is controlled to maintain a fixed gas pressure in the body cavity.

So as to give an indication when for some reason a critical pressure is reached or exceeded in the body cavity, the pressure switch may control a second valve by which an alarm device is pneumatically actuated, or alternatively the contact-equipped pressure gauge may be fitted with a second pair of contacts by which an alarm device is actuated.

DESCRIPTION OF THE PREFERRED EMBODIMENTS

Figure 1:
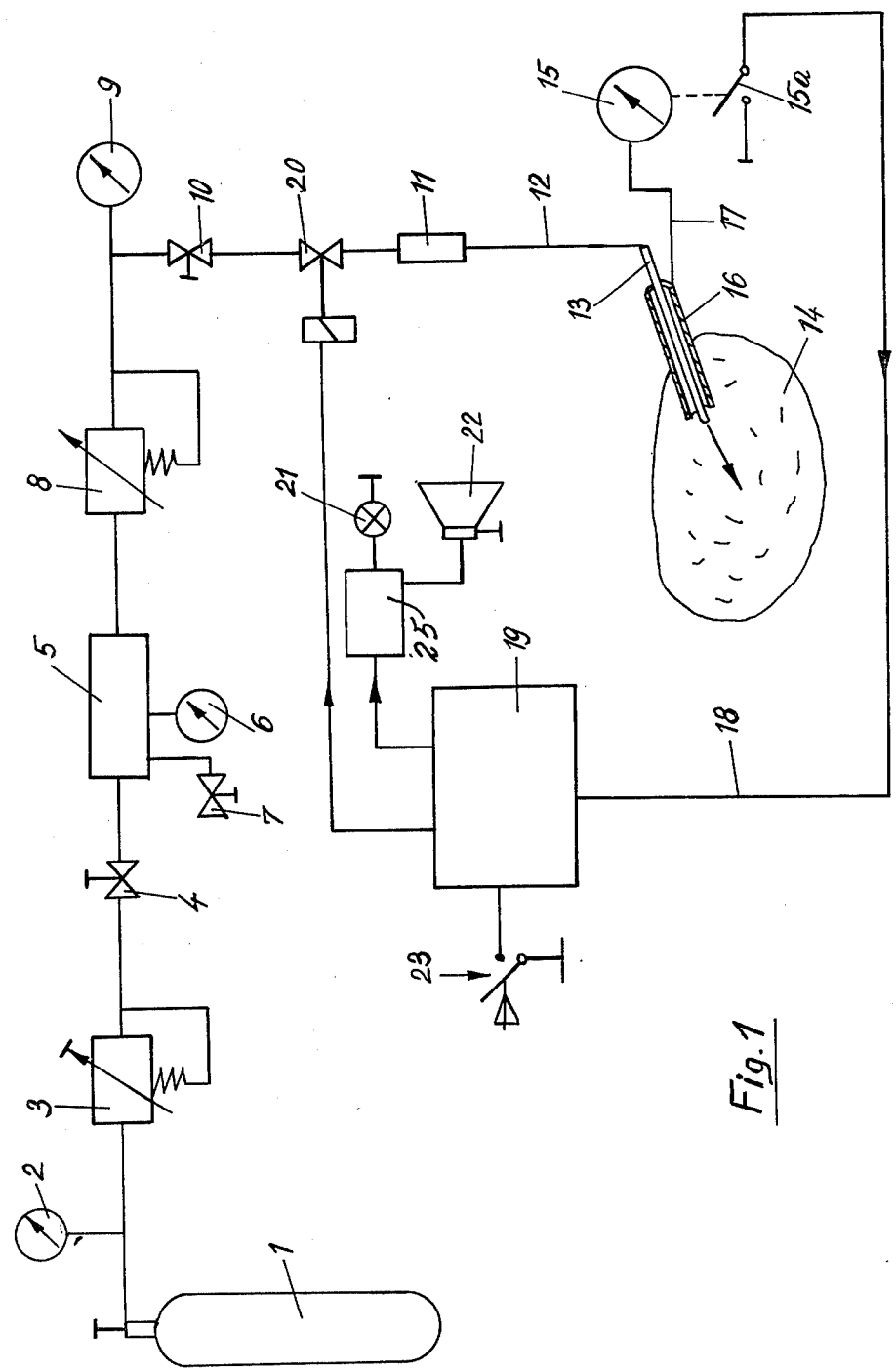
FIG. 1 is a diagram of a gas insufflation apparatus in which the gas pressure in the body cavity can be set at a preselected level and which has an alarm arrangement.

The insufflation apparatus shown in FIG. 1 includes in a known fashion a compressed gas bottle 1 containing a fairly large quantity of gas, e.g. carbon dioxide or nitrous oxide gas, the pressure from which is controlled and monitored by a pressure gauge 2 and a pressure reducer 3. From the pressure reducer 3 the gas flows at reduced pressure via a shut-off valve 4 to an intermediate container 5 the pressure and quantity of gas in which can be read off from a pressure gauge 6. Container 5 is also provided with a safety valve 7.

In accordance with the invention, the reduced-pressure insufflation gas from container 5 flows through a pressure regulator 8, which is advantageously continuously adjustable and by means of which the desired gas pressure in the body cavity required by a particular patient can be preselected. The regulated pressure can be monitored by a pressure gauge 9. To inject a volume of gas into the body cavity, a valve 10 downstream of the pressure regulator 8 is opened manually so that the gas will then flow to the schematically indicated body cavity 14, advantageously via a rate of flow controller 11, an insufflation duct 12 and a tube constituted by a canula 13, the preselected pressure being maintained by pressure regulator 8.

When this is done an accident or defect in the apparatus may cause the critical preselected gas pressure in the body cavity to be exceeded and so that this is at once indicated and the gas pressure held down the body cavity 14 is connected via a measuring duct to a contact-equipped pressure gauge 15. The measuring duct consists of a tube which runs alongside the canula 13 or of an outer shell 16 which surrounds the canula at a distance from it, this tube or shell opening distally into the body cavity and being connected proximally via a pipe 17 to the contact-equipped pressure gauge 15. The contact-equipped pressure gauge 15 is fitted with a limit contact 15a which is set to an alarm pressure, i.e. a critical pressure for the particular body cavity, and this limit contact 15a is connected via line 18 to a bi-stable alarm control circuit 19 which closes a solenoid valve 20 in the insufflation duct as soon as an alarm or critical pressure is reached in the body cavity and the control function of the contact-equipped pressure-gauge 15, 15a is triggered. At the same time, the alarm circuit 25 actuates a visual alarm 21 and/or an audio alarm 22. The alarm signal can be turned off by means of a switch 23.

Figure 2:
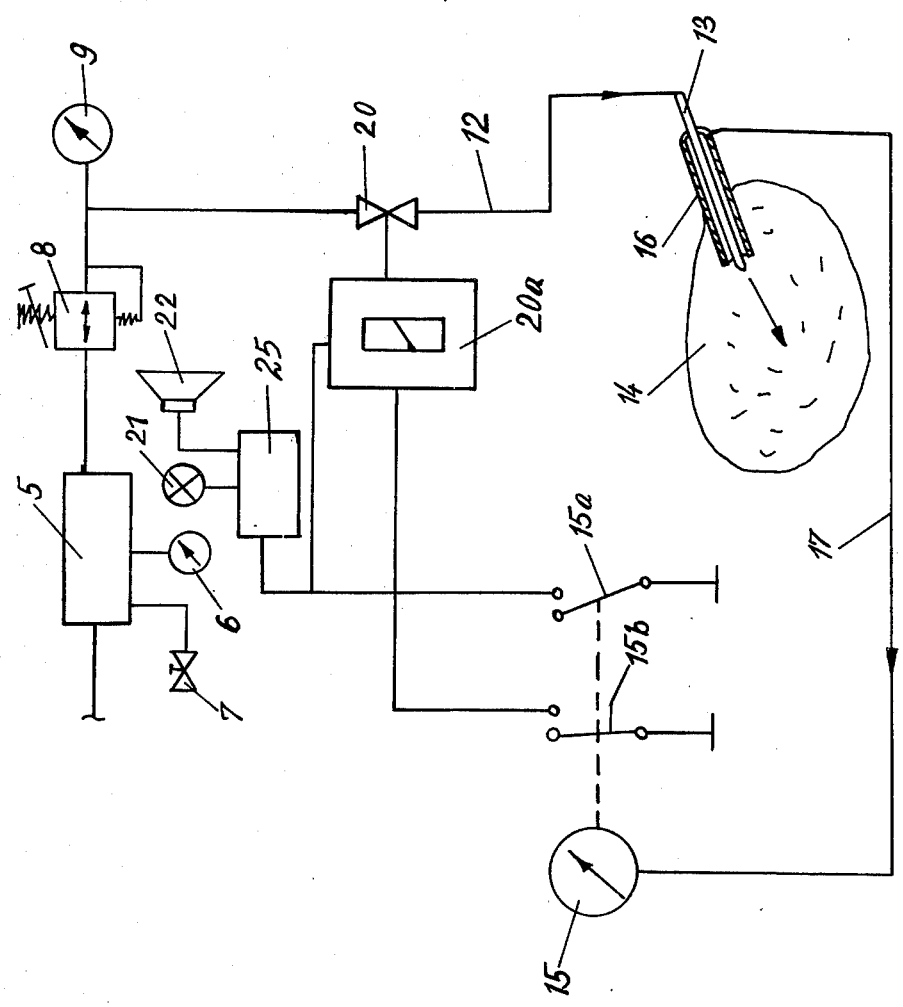
FIG. 2 is a diagram of a modified embodiment for maintaining a preselected gas pressure in the body cavity.

In the modified embodiment of the invention shown in FIG. 2, from which parts 1 to 4 in FIG. 1 have not been shown, it is also possible to set the pressure-regulator 8 to the maximum possible body-cavity pressure and the contact-equipped pressure-gauge 15 is provided with an additional second pair of contacts 15b which can be set to the desired preselected body-cavity pressure. This pair of contacts 15b is closed by the pressure gauge 15 as soon as the pressure in the body cavity rises above the selected pressure and as a result a solenoid valve 20 in the insufflation duct is closed via a controlling device 20a. If the pressure in the body cavity drops below the selected level the pair of contacts 15b opens and so also does solenoid valve 20 and as a result more insufflation gas flows into the body cavity until the preset pressure is again reached in the body cavity. In this embodiment also the alarm circuit 25 is actuated by closure of the first mentioned pair of contacts 15a of the contact-equipped pressure gauge 15 as soon as any defect causes the gas pressure in the body cavity to reach or exceed a critical pressure, at which time the alarm circuit closes valve 20 via controller 20a, if it has not already been closed by the contacts 15b as they exert their control function. At the same time a visual or audio signal is triggered.

Figure 3:
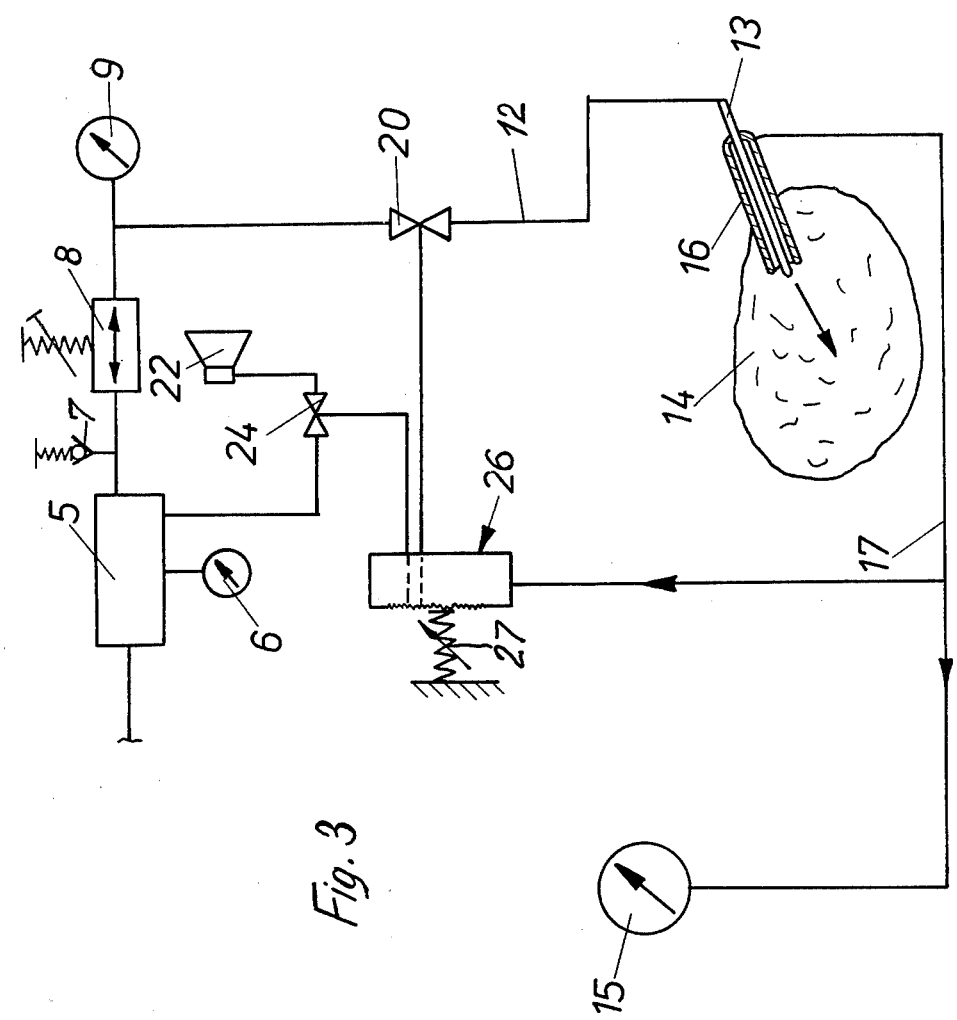
FIG. 3 is a diagram of another modified embodiment for maintaining a preselected gas pressure in the body cavity.

In order to avoid delicate and expensive contact-equipped pressure-gauges and so as to be able to use conventional, mechanically or pneumatically operated controllable valves in the insufflation duct, in a particularly advantageous embodiment which is shown in FIG. 3, compressed gas from a compressed gas source 1 (not shown) and a pressure reducer 3 (not shown) is fed to an intermediate container 5, the pressure of the gas in which, and thus its amount, can once again be read off from a pressure gauge 6. The container 5 is provided with a safety valve 7. The pressure reducer 8 which can be set to a fixed value, brings the gas to the maximum permissible pressure for the patient. Downstream of pressure reducer 8, the gas is fed via a valve 20 into the canula 13 which is to be inserted in the body cavity 14. Valve 20 can be pneumatically operated by a pressure switch 26 which can be set to the pressure required in the body cavity. The pressure switch 26 is known per se and by means of its diaphragm, which responds to the gas pressure in the body cavity and is advantageously able to be set by resilient means for example by tightening and releasing the illustrated spring 27 it directly controls the valve 20 in the insufflation duct 12 to the canula 13 so that the desired gas pressure is maintained in the body cavity.

Alongside the canula 13 is provided the measuring duct 17 already mentioned which opens into the body cavity. To one end of the measuring duct 17 is connected a pressure monitoring gauge 15 and to its other end is connected the pressure switch 26 which can be set to the gas pressure required in the body cavity. If the pressure in the body cavity drops below the required level, the pressure switch 26 will open valve 20 directly, and will close it again once the pressure which has been set is reached in the body cavity.

If as a result of a defect or for any other reason a critical gas pressure is reached or exceeded in the body cavity, the resulting increased movement of the diaphragm in pressure switch 26 directly opens a second valve 24 and this second valve connects a pneumatically operated alarm 22 to the intermediate container 5 and thus triggers an alarm.

We claim:

1. A gas insufflation apparatus for filling a body cavity with intracorporeal insufflating gas at a constant pressure level and maintaining the pressure of the gas within the body cavity constantly at a single fixed pre-selected pressure level, said apparatus comprising:
    (a) a source of compressed insufflating gas which is either carbon dioxide or nitrous oxide;
    (b) an insufflation duct connected to said compressed gas source and canula means connected to said insufflation duct insertable into the body cavity for introducing the gas thereinto;
    (c) measuring duct means insertable into the body cavity or receiving gas from the body cavity thereby to measure the intracorporeal gas pressure;
    (d) a solenoid valve interposed in said insufflation duct and electrical circuit means for automatically controlling said solenoid valve for admitting a flow of the compressed gas, and shutting off the flow of compressed gas, in said insufflation duct;
    (e) a variable pressure regulator interposed in the insufflation duct between the source of compressed gas and said valve by means of which a desired body cavity pressure may be pre-selected; and
    (f) pressure sensitive switch means responsive to pressure in said measuring duct and having normally open contacts interposed in said circuit means said contacts being set to close at a predetermined intracorporeal pressure thereby completing the circuit to said solenoid valve solely in response to an upper deviation from said predetermined pressure of the gas in said body cavity.

2. A gas insufflation apparatus according to claim 1, wherein said measuring duct comprises a tubular member disposed along side said canula, said tubular member having a distal end which opens into the body cavity and having a proximal end connected to said pressure sensitive switch means for communicating the intracorporeal gas pressure which controls said pressure sensitive switch means.

3. A gas insufflation apparatus according to claim 1, wherein said measuring duct comprises a shell-like member which surrounds said canula in spaced relationship thereto, said shell-like member having a distal end which opens into the body cavity and having a proximal end connected to said pressure sensitive switch means for communicating intracorporeal gas pressure for controlling said pressure sensitive switch means.

4. An insufflation apparatus as claimed in claim 1, and further comprising a gas supply line connecting said insufflation duct to said compressed gas source, a pressure gauge in the gas supply line for measuring the pressure of the gas of said compressed gas source, a pressure reducer connected in said gas supply line upstream of said pressure gauge, a shut-off valve connected in said gas supply line downstream of said pressure reducer, an intermediate gas container connected in said gas supply line downstream of said shut-off valve, said intermediate container having a safety valve, a gauge for indicating the pressure and quantity of gas in said intermediate container, a pressure regulator connected to said intermediate container and connected in said gas supply line downstream of said insufflation duct, a manually operable valve connected in the supply line for admitting insufflation gas into the insufflation duct between said solenoid valve therein and said canula, and a pressure gauge connected to said measuring duct means for monitoring the pressure of the gas supplied to the body cavity.

5. Insufflation apparatus according to claim 4 in which the last-named pressure gauge includes means operably connected to said pressure sensitive switch means.

6. Insufflation apparatus according to claim 1 in which the pressure sensitive switch means is selectively settable to a pre-selected intracorporeal gas pressure.

7. Insufflation apparatus according to claim 1 comprising second valve means operatively responsive to said pressure sensitive switch means and a pnuematically operated alarm device, said second valve means connecting said alarm device to said gas supply duct when the gas pressure in the body cavity is critical or too high.

8. Insufflation apparatus according to claim 1 and comprising an alarm, a pressure gauge connected to said measuring duct means, said pressure sensitive switch means communicating with said pressure gauge, said pressure sensitive switch means comprising two pairs of contacts of which one pair of contacts opens or closes the circuit of said solenoid valve when the pressure in the body cavity deviates from the preselected pressure and of which the other pair of contacts operates said alarm as soon as the gas pressure in the body cavity reaches a critical level.

9. A gas insufflation apparatus for filling a body cavity with intracorporeal insufflating gas at a constant pressure level and maintaining the pressure of the gas within the body cavity constantly at a single fixed preselected pressure level, said apparatus comprising:
   (a) a source of compressed insufflating gas which is either carbon dioxide or nitrous oxide;
   (b) an insufflation duct connected to said compressed gas source and canula means connected to said insufflation duct and insertable into the body cavity for introducing the gas thereinto;
   (c) measuring duct means insertable into the body cavity for receiving gas from the body cavity thereby to measure the intracorporeal gas pressure;
   (d) a normally open electrically controlled valve in communication with said insufflation duct for automatically admitting a flow of the compressed gas, and shutting off the flow of compressed gas to said insufflation duct when closed;
   (e) a variable pressure regulator interposed in the insufflation duct between the source of compressed gas and said valve by means of which a desired body cavity pressure may be pre-selected; and
   (f) pressure sensitive switch means responsive to intracorporeal pressure in said measuring duct and means electrical circuit responsive to said pressure sensitive switch means for closing said controlled valve at a predetermined intracorporeal pressure in response to an upper deviation from said predetermined pressure of the gas in said body cavity.

10. A gas insufflation apparatus according to claim 9, wherein said measuring duct comprises a tubular member disposed along side said canula, said tubular member having a distal end which opens into the body cavity and having a proximal end connected to said pressure sensitive switch means for communicating the intracorporeal gas pressure which controls said pressure sensitive switch means.

11. A gas insufflation apparatus according to claim 9, wherein said measuring duct comprises a shell-like member which surrounds said canula in spaced relationship thereto, said shell-like member having a distal end which opens into the body cavity and having a proximal end connected to said pressure sensitive switch means for communicating intracorporeal gas pressure for controlling said pressure sensitive switch means.

12. An insufflation apparatus as claimed in claim 9, and further comprising a gas supply line connecting said insufflation duct to said compressed gas source, a pressure gauge in the gas supply line for measuring the pressure of the gas of said compressed gas source, a pressure reducer connected in said gas supply line upstream of said pressure gauge, a shut-off valve connected in said gas supply line downstream of said pressure reducer, an intermediate gas container connected in said gas supply line downstream of said shut-off valve, said intermediate container having a safety valve, a gauge for indicating the pressure and quantity of gas in said intermediate container, a pressure regulator connected to said intermediate container and connected in said gas supply line downstream of said insufflation duct, a manually operable valve connected in the supply line for admitting insufflation gas into the insufflation duct, a flow control device in said insufflation duct between said solenoid valve therein and said canula, and a pressure gauge connected to said measuring duct means for monitoring the pressure of the gas supplied to the body cavity.

13. Insufflation apparatus according to claim 12 in which the last named pressure gauge includes means operably connected to said pressure sensitive switch means.

14. Insufflation apparatus according to claim 9 in which the pressure sensitive switch means is selectively settable to a pre-selected intracorporeal gas pressure.

15. Insufflation apparatus according to claim 9 comprising second valve means operatively responsive to said pressure sensitive switch means and a pneumatically operated alarm device, said second valve means connecting said alarm device to said gas supply duct when the gas pressure in the body cavity is critical or too high.

* * * * *

UNITED STATES PATENT AND TRADEMARK OFFICE
CERTIFICATE OF CORRECTION

PATENT NO. : 4,207,887
DATED : June 17, 1980
INVENTOR(S) : Siegfried Hiltebrandt and Helmut Wurster It is certified that error appears in the above-identified patent and that said Letters Patent are hereby corrected as shown below:

On the Title Page Item (30) should read

-- [30] Foreign Application Priority Data

Oct. 4, 1975    Germany    2544467

Apr. 10, 1976    Germany    2615736    --.

Signed and Sealed this

Twenty-third Day of December 1980

[SEAL]

Attest:

SIDNEY A. DIAMOND

Attesting Officer    Commissioner of Patents and Trademark